(12) United States Patent
Bachmann et al.

(10) Patent No.: US 9,913,939 B2
(45) Date of Patent: Mar. 13, 2018

(54) VALVE ARRANGEMENT FOR USE IN AN EXTRACORPOREAL BLOOD CIRCUIT AND METHOD

(75) Inventors: Angelika Bachmann, Rosbach v.d.H. (DE); Michael Herrenbauer, Neu-Anspach (DE); Wolfgang Wehmeyer, Tuebingen (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 519 days.

(21) Appl. No.: 13/698,192

(22) PCT Filed: May 16, 2011

(86) PCT No.: PCT/EP2011/002412
§ 371 (c)(1),
(2), (4) Date: Dec. 12, 2012

(87) PCT Pub. No.: WO2011/144315
PCT Pub. Date: Nov. 24, 2011

(65) Prior Publication Data
US 2013/0110028 A1    May 2, 2013

(30) Foreign Application Priority Data
May 18, 2010 (DE) .......................... 10 2010 020 838

(51) Int. Cl.
*A61M 1/30* (2006.01)
*A61M 1/16* (2006.01)
(Continued)

(52) U.S. Cl.
CPC ................ *A61M 1/30* (2013.01); *A61M 1/16* (2013.01); *A61M 1/1605* (2014.02); *A61M 1/34* (2013.01);
(Continued)

(58) Field of Classification Search
CPC .................................. A61M 1/30; A61M 1/16
See application file for complete search history.

(56) References Cited

U.S. PATENT DOCUMENTS

| 4,209,402 | A |   | 6/1980 | Gentles |
|-----------|---|---|--------|---------|
| 5,863,421 | A | * | 1/1999 | Peter et al. .................... 210/134 |

(Continued)

FOREIGN PATENT DOCUMENTS

| DE | 8904529 U1  | 5/1989 |
|----|-------------|--------|
| DE | 10046651 A1 | 4/2002 |

(Continued)

OTHER PUBLICATIONS

International Search Report from PCT/EP2011/002412 dated Oct. 31, 2011.

*Primary Examiner* — Tatyana Zalukaeva
*Assistant Examiner* — Sara Sass
(74) *Attorney, Agent, or Firm* — Fish & Richardson P.C.

(57) ABSTRACT

The present invention relates to a valve arrangement for use in an extracorporeal blood circuit having at least one arterial blood line and at least one venous blood line, the valve arrangement having at least one first valve arranged in the arterial blood line, a second valve arranged in the venous blood line, a fourth valve arranged in a first arteriovenous connection line between the arterial blood line of the circuit and the venous blood line of the circuit, and a fifth valve arranged in a second arteriovenous connection line between the arterial blood line and the venous blood line; and/or a third valve arranged for establishing a fluid connection in a blood line between the arterial blood line and the venous blood line of the circuit; and/or a sixth valve arranged between a blood treatment device and an air venting device of the circuit.

25 Claims, 6 Drawing Sheets (51) Int. Cl.
  *A61M 37/00* (2006.01)
  *A61M 1/36* (2006.01)
  *A61M 39/22* (2006.01)
  *A61M 1/34* (2006.01)
  *A61M 39/00* (2006.01)

(52) U.S. Cl.
  CPC .......... *A61M 1/3403* (2014.02); *A61M 1/365* (2014.02); *A61M 1/3607* (2014.02); *A61M 1/3643* (2013.01); *A61M 1/3644* (2014.02); *A61M 1/3646* (2014.02); *A61M 1/3647* (2014.02); *A61M 1/3649* (2014.02); *A61M 39/22* (2013.01); *A61M 2039/0018* (2013.01); *A61M 2205/3331* (2013.01); *A61M 2205/3344* (2013.01); *A61M 2205/50* (2013.01); *A61M 2205/52* (2013.01)

(56) References Cited

U.S. PATENT DOCUMENTS

| | | | |
|---|---|---|---|
| 5,957,879 A | 9/1999 | Roberts et al. | |
| 6,177,049 B1 | 1/2001 | Schnell et al. | |
| 6,189,388 B1 | 2/2001 | Cole et al. | |
| 6,491,656 B1 * | 12/2002 | Morris | 604/6.09 |
| 6,890,316 B2 * | 5/2005 | Rawles | A61M 1/1698 604/264 |
| 2003/0018290 A1 | 1/2003 | Brugger et al. | |
| 2004/0084371 A1 | 5/2004 | Kellam et al. | |
| 2004/0084647 A1 | 5/2004 | Beden et al. | |
| 2009/0221949 A1 * | 9/2009 | Allers | A61M 1/3621 604/6.16 |
| 2011/0070132 A1 | 3/2011 | Haecker et al. | |
| 2011/0230772 A1 | 9/2011 | Koball et al. | |
| 2012/0080437 A1 | 4/2012 | Guenther et al. | |
| 2012/0086933 A1 | 4/2012 | Spruck et al. | |

FOREIGN PATENT DOCUMENTS

| | | |
|---|---|---|
| DE | 10239597 A1 | 3/2004 |
| DE | 102009024468 A1 | 2/2010 |
| DE | 10 2008 059379 A1 | 6/2010 |
| DE | 102009012632 A1 | 9/2010 |
| DE | 102009024464 A1 | 12/2010 |
| JP | 2007236564 A | 9/2007 |
| JP | 2008012210 A | 1/2008 |
| WO | 2008/028579 A1 | 3/2008 |

* cited by examiner

VALVE ARRANGEMENT FOR USE IN AN EXTRACORPOREAL BLOOD CIRCUIT AND METHOD

CROSS REFERENCE TO RELATED APPLICATIONS

This is a 371 national phase application of PCT/EP2011/002412 filed May 16, 2011, which claims priority from German Patent Application No. 10 2010 020 838.8, filed May 18, 2010.

FIELD OF INVENTION

The present invention relates to a valve arrangement for use in an extracorporeal blood circuit. It further relates to a blood tubing set, a blood cassette, a treatment apparatus, a method, a digital storage means, a computer program product, and a computer program.

BACKGROUND OF INVENTION

Extracorporeal blood circuits for use in an extracorporeal treatment of body fluids such as blood are known from practice. Prior to their first use, such blood circuits are regularly filled with a liquid in order to displace air contained therein. After termination of the treatment, they are regularly filled with a fluid in order to return blood present in the extracorporeal blood circuit upon termination of the treatment back to the vascular system of the patient.

One object of the present invention is to propose a new valve arrangement enabling short-circuiting the arterial and the venous line of the extracorporeal blood circuit, filling the blood circuit and/or emptying the said. Additionally, corresponding methods are to be proposed.

Thus, according to the present invention, there is proposed a valve arrangement which is suited and/or provided and/or configured for its use in an extracorporeal blood circuit, comprising at least one arterial blood line and at least one venous blood line. The valve arrangement comprises at least one first valve which is arranged in the arterial blood line, a second valve which is arranged in the venous blood line, a fourth valve which is arranged in a first arteriovenous connection line between the arterial blood line of the extracorporeal blood circuit and the venous line of the extracorporeal blood circuit as well as a fifth valve which is arranged in a second arteriovenous connection line between the arterial blood line and the venous blood line.

Alternatively or additionally to the afore-mentioned valves, the valve arrangement according to the present invention comprises a third valve which is arranged for establishing a fluid connection in a blood line between the arterial blood line and the venous blood line of the extracorporeal blood circuit or which is arranged for establishing a fluid connection directly between the arterial blood line and the venous blood line, preferably without a tube element being connected there between.

In turn additionally to some or all of the aforementioned valves or instead of the same, the valve arrangement according to the present invention comprises a sixth valve which is arranged between a blood treatment device or means, respectively, and an air venting or deflating or air dumping means or device, respectively, of the extracorporeal blood circuit.

The blood tubing set according to the present invention as well as the blood cassette according to the present invention comprise at least one valve arrangement according to the present invention.

The treatment apparatus according to the present invention is provided for extracorporeally treating medical fluids, in particular blood. It comprises at least one controlling device or means, respectively, as well as actuators that are provided and configured for controlling or regulating at least one valve arrangement according to the present invention.

Advantageous embodiments of the present invention are each subject matter of the dependent claims.

Embodiments according to the present invention can comprise some or all of the following features in an arbitrary combination.

In some embodiments according to the present invention, the blood treatment device is a blood filter.

In certain embodiments according to the present invention, the air venting device is a drip chamber or a venting site or a part thereof, respectively.

In some embodiments according to the present invention, the arterial blood line of the extracorporeal blood circuit is a line conducting blood with higher oxygen content during the blood treatment (as compared to the venous blood line which is conducting blood with lower oxygen content).

In certain embodiments according to the present invention, the arterial blood line of the extracorporeal blood circuit is a line which, during the blood treatment, conducts blood from the patient whereas the venous blood line conducts blood to the patient.

In some embodiments according to the present invention, the arterial blood line of the extracorporeal blood circuit is a line or patient line which, during the blood treatment, conducts blood between a patient connector and the blood filter. In certain embodiments according to the present invention, the venous blood line is a line or patient line which conducts blood between a drip chamber and a patient connector.

In some embodiments according to the present invention, the first and/or the second arteriovenous blood line is designed as a fluid connection, for example, as a tube segment, a line or the like, allowing blood to flow through from an arterial blood line to a venous blood line of the extracorporeal blood circuit, respectively, independently from the direction in which the flow takes place.

In certain embodiments according to the present invention, the valve arrangement additionally comprises at least one ventilation valve for venting the blood circuit, in particular by establishing a connection between an interior of the extracorporeal blood circuit and an exterior thereof, e.g., the atmosphere.

In some embodiments according to the present invention, some or all of the afore-mentioned valves are active valves.

An active valve in the sense of the present invention is in certain embodiments according to the present invention a valve which is, in particular exclusively, provided for active actuation, independently from the actuation being performed manually or by means of appropriate devices or means, respectively. In these embodiments, an active valve thus differs from a valve opening or closing in a self-actuating or automatic, respectively, manner such as, e.g., a non-return valve.

An active valve in the sense of the present invention is in certain embodiments according to the present invention a valve which is, in particular exclusively, controlled or actuated by a device such as, e.g., a controller.

In certain embodiments according to the present invention, the valve arrangement comprises a device for controlling or regulating the valve function of all or some of the aforementioned valves.

In some embodiments according to the present invention of the valve arrangement, the valve arrangement is designed and provided for use with a non-occluding pump for conveying the fluid to be treated, in particular blood.

In certain embodiments according to the present invention of the valve arrangement, at least the first, the second, the fourth and the fifth valve are present in a common support material. A support material in the sense of the present invention is in certain embodiments a single element or component, respectively, a smallest non-destructively available unit, a blood cassette, an adaptor or a device or means, respectively, generally provided for connecting arterial and venous patient lines or connectors or the like.

In certain embodiments, the valve arrangement according to the present invention comprises at least one recirculation adaptor or is at least partially part of such a recirculation adaptor. In these embodiments, the recirculation adaptor comprises at least four valves, in particular, the first, the second, the fourth and the fifth valve. In certain embodiments, the recirculation adaptor further comprises the third valve.

In some embodiments according to the present invention of the valve arrangement, at least the third valve is designed as a phantom valve.

A "phantom valve" as used herein can be a component comprising an actuator surface (for example, an actuator membrane) reachable by means of an actuator which can fulfill the function of a valve. Examples for appropriate phantom valves can be derived from the applications of the present applicant DE 10 2009 024 664.6 which has been deposited at the German Patent and Trademark Office on Apr. 23, 2009, DE 10 2009 024 468.9 which has been deposited at the German Patent and Trademark Office on Jun. 10, 2009 or DE 10 2009 012 632.5 which has been deposited at the German Patent and Trademark Office on Mar. 10, 2009, the entire contents of which are hereby each fully incorporated by way of reference.

In certain embodiments according to the present invention, the valve arrangement comprises sensors for measuring the arterial pressure in front of the filter means, e.g., a dialyzer, ("pre filter pressure"), for measuring the venous pressure downstream the air venting device, e.g., an air separation chamber, ("pressure return"), for measuring the optical density, for detecting the air bubbles present in a blood line interior of the arterial or the venous blood line ("air bubble detector", or "ABD") and the like as well as arbitrary combinations thereof. The sensors can be present in or at the arterial and/or the venous blood line. They can be present in or at the arterial and/or the venous leg of the extracorporeal blood circuit. The sensors can be designed as multi-sensors for measuring/detecting several of the aforementioned parameters.

In some embodiments according to the present invention, the valve arrangement comprises a device for controlling or regulating a flow difference which is generated by means of setting or operating a blood pump and/or a dialysate pump and/or appropriate means such as valves, throttles and the like, in particular in an intended manner.

In certain embodiments according to the present invention, the valve arrangement is designed in a blood cassette or is part of such a blood cassette or comprises such a blood cassette. Such a blood cassette can, for example, be designed as a cast part or an injection molded part. It can independently thereof be designed as a disposable.

In some embodiments according to the present invention of the valve arrangement, one, two or more valves are designed as being switchable as a segment of a rotatable or rotational element, respectively. Thereby, the respective rotatable elements can be designed as being actuable independently from each other or in a coupled manner, i.e. only in common.

In certain embodiments, the treatment apparatus according to the present invention is designed as an extracorporeal treatment apparatus, in particular as a dialyzing apparatus, particularly as a hemodialysis apparatus, a hemofiltration apparatus, a hemodiafiltration apparatus or as an apparatus for the adsorption, liver support therapy, apheresis, transfusion etc. It is particularly apt for use in methods in which the fluid is drawn from the patient and is returned back to the patient by means of different needles or accesses (the latter are known as double needle methods).

The object of the present invention is further solved by a method for handling an extracorporeal blood circuit, using a valve arrangement according to the present invention. The handling of the extracorporeal blood circuit can comprise or respectively consist of short-circuiting an arterial and a venous blood line of the extracorporeal blood circuit, filling the extracorporeal blood circuit and/or flushing sections or parts of the extracorporeal blood circuit while a flow disturbance is present or is not present in one of the blood lines of the extracorporeal blood circuit, as well as arbitrary combinations thereof.

In some embodiments, the method for handling according to the present invention serves for short-circuiting an arterial blood line and a venous blood line of an extracorporeal blood circuit by means of a valve arrangement according to the present invention by connecting the arterial blood line with the venous blood line by means of opening the third valve.

In some embodiments, the method for handling according to the present invention serves for filling or priming an extracorporeal blood circuit or parts thereof by means of a valve arrangement according to the present invention when using an occluding blood pump. This method can comprise the following steps—solitarily or in an arbitrary combination: connecting the extracorporeal blood circuit with an occluding blood pump; connecting a dialysate circuit with a dialysate pump; filling the dialysate circuit with fluid; conveying a flow by means of the blood pump in a direction opposite to the usual flow direction of an extracorporeal blood treatment; conveying a flow across the membrane of a filter of a blood treatment apparatus by means of the dialysate pump, wherein the flow is larger than the flow conveyed or generated by the blood pump, while the first and the second valve are open; opening a ventilation valve; stopping the dialysate pump or setting a balancing system to neutral balance and closing the ventilation valve; circulating the fluid by means of the blood pump within the extracorporeal blood circuit in usual flow direction while the first and the second valve are still open; removing air from the extracorporeal blood circuit by means of an air separation chamber by setting a positive balance, i.e. by generating a flow generated by means of the dialysate pump of larger than zero, in the balancing system while the ventilation valve is open.

According to the present invention, in some embodiments of the present invention, a "usual" flow direction is understood as the usual flow direction of an extracorporeal blood treatment.

Thereby, the usual flow direction of an extracorporeal blood treatment can be the direction in which the blood is flowing extracorporeally most of the time.

The usual flow direction of an extracorporeal blood treatment can be the direction in which the blood is flowing extracorporeally from the arterial vascular access of the patient by means of the arterial patient line or blood line and to the venous vascular access of the patient by means of the venous patient or blood line in a double needle method.

Thereby, the flows QD (dialysate) and QB (blood) can preferably be determined such that venting a blood line between a filter of a blood treatment apparatus and the air separation chamber and the arterial blood line and the venous blood line is achieved at the same time.

Furthermore, the afore-mentioned steps of stopping the dialysate pump or setting a balancing systems to neutral balance and closing the ventilation valve, circulating and removing air can hereby be performed for several times.

In some embodiments, the flow QD is to be understood as the dialysate flow out of the dialysate compartment of the dialyzer through the membrane into the blood compartment of the dialyzer.

In some embodiments according to the present invention, QD is thus to be differed from the entire flow of the dialysate which is pumped into the dialysate compartment of the dialyzer by means of the dialysate pump.

In certain embodiments according to the present invention the flow of the dialysate in front of and behind the dialyzer is balanced (e.g., by means of known balancing chambers, not shown in the figures).

Appropriate devices or means, respectively, and/or methods or processes or proceedings, respectively, can be used for balancing.

Balancing during an extracorporeal blood treatment can be of interest or importance in particular in embodiments in which a defined amount of excess water is to be removed from the patient, for example, during a dialysis.

In some embodiments according to the present invention, a "neutral balance" is understood such that the pressures and flows in front of and behind the dialysate compartment and in the blood compartment are set such that no flow QD of the dialysate is pressed through the membrane. This can, for example, be performed by completely stopping the dialysate pump. Stopping or completely stopping is, however, not mandatorily required herefor.

Thus, in certain embodiments, the fluid flow to the patient at a neutral balance is as high as the fluid flow away from the patient. The patient's weight can thus—substantially or completely—remain constant.

In some embodiments of the present invention, a "positive balance" is in contrary defined such that a flow QD of the dialysate is larger than zero, i.e., QD>0. When QD>0, dialysate passes through the membrane into the blood compartment. In other words, the pressures and flows in the dialysate system in front of and behind the dialysate compartment and in the blood compartment are set such that a flow QD of the dialysate is forced or compelled, respectively, out of the dialysate compartment through the membrane into the blood compartment.

In certain embodiments, at a positive balance, the fluid flow to the patient is thus higher than the fluid flow away from the patient. Thus, at a positive balance, the patient can be supplied with liquid.

The desired "balance" can be set, e.g., according to a predetermined program by the blood treatment apparatus's control.

Independently from setting a positive or a neutral balance, in some embodiments according to the present invention, qualitative ratios between QD and QB can be or will be predetermined for the single rinsing procedures. Based on such a ratio, the "balance" can, but does not have to, be influenced under certain circumstances. In certain embodiments according to the present invention, setting the ratio between QD and QB can serve for setting certain flows in the arterial and/or the venous line and the valve arrangement according to the present invention (also referred to as a "rinsing adaptor").

According to the present invention, the method for handling can be or comprise filling the extracorporeal blood circuit or parts thereof when using a non-occluding blood pump. This method comprises at least one of the steps of: short-circuiting patient connectors; introducing or supplying, respectively, fluid from a dialysate circuit into the extracorporeal blood circuit by means of setting a positive balance; stopping the blood pump; closing a sixth valve, opening the first and the second valve as well as the ventilation valve; closing the third, fourth and fifth valve, if present; pressing fluid out of the dialysate compartment across the membrane of the filter onto the blood side of the filter; closing the first and the second valve; opening the sixth valve after having detected a fluid level in the air separation chamber; stopping the dialysate pump and/or setting the balancing system to a neutral balance; closing the ventilation valve; circulating the fluid within the extracorporeal blood circuit by means of the blood pump while the first and the second valve as well as the sixth valve are open; setting a positive balance in the balancing system (QD>0); opening the ventilation valve; and stopping the blood pump.

Some of these method steps can be performed for several times.

According to the present invention, the method for handling an extracorporeal blood circuit by means of the valve arrangement according to the present invention can be or comprise flushing an extracorporeal blood circuit or parts thereof by means of a valve arrangement according to the present invention, while no flow disturbance is present in one of the blood lines. The method then comprises at least one of the steps of: conveying a flow by means of the blood pump in a direction opposite to the usual flow direction while the blood lines are connected to the vascular access of the patient; conveying fluid by means of the dialysate pump out of the dialysate circuit with a flow being larger than the flow generated by means of the blood pump across the membrane of a filter of a blood treatment apparatus into the extracorporeal blood circuit; opening the first and the second valve, opening the sixth valve while the third, the fourth and the fifth valve and the ventilation valve are closed, as far as they are present; determining, by means of sensors, when or that the fluid displaces or has sufficiently displaced blood; controlling or regulating the blood return process according to the amount of the flow difference between the flow generated or conveyed by means of the dialysate pump and the flow generated or conveyed by means of the blood pump or by correspondingly switching the first and the second valve; stopping the non-occluding blood pump; switching the first and the second valve in order to induce or prompt, respectively, the blood return via a selected one of the blood lines.

According to the present invention, the method for handling an extracorporeal blood circuit can be or comprise flushing the extracorporeal blood circuit or parts thereof, while a flow disturbance is present in one of the blood lines. The method then comprises at least one of the steps of: conveying by means of the blood pump with a flow in a direction opposite to the usual flow direction, wherein the arterial blood line and/or the venous blood line are each connected with the respective vascular access of the patient; conveying fluid out of the dialysate circuit across the membrane of a filter of a blood treatment apparatus into the extracorporeal blood circuit by means of a dialysate pump with a flow that is larger than the flow generated by means of the blood pump; directing the entire flow to one of the two blood lines by correspondingly switching the first, the second, the third, the fourth and/or the fifth valve; switching the fifth valve and the sixth valve or adequately selecting the flow difference between the flow conveyed by means of the dialysate pump and the flow conveyed by means of the blood pump for achieving a flow through the arterial blood line or the venous blood line.

Moreover, in the method according to the present invention, a flow QD can be generated in the extracorporeal blood circuit by means of the dialysate pump while the blood pump does not convey or stagnates or is not overflown or flushed, respectively.

Furthermore, in certain embodiments of the method according to the present invention, the blood pump and the dialysate pump convey with the same pump flow rates wherein the blood pump preferably rotates or conveys, respectively, in reverse direction.

According to the present invention, the term "reverse" or "reverse direction", respectively, is in connection with the direction of conveyance of the blood pump and/or of the dialysate pump to be understood as a direction opposite to the direction of conveyance of the respective pump in which the respective pump is predominantly conveying during a proceeding blood treatment or a direction opposite to the usual direction of conveyance of a proceeding blood treatment.

In certain embodiments, the method according to the present invention further comprises setting a positive balance wherein the flow conveyed by means of the dialysate pump is larger than the flow conveyed by means of the blood pump when using a non-occluding blood pump and/or switching the flow paths by means of the first to fifth valves as well as the sixth valve in order to flush the non-blocked blood lines.

All advantages achievable by means of the valve arrangement according to the present invention may undiminishedly also be obtained by the method according to the present invention and vice versa.

The object according to the present invention is further solved by a digital storage means in connection with corresponding hardware suited and/or provided therefor, a computer program product and a computer program. All advantages achievable by means of the method according to the present invention may undiminishedly also be obtained by means of the digital storage means according to the present invention, the computer program product according to the present invention and/or the computer program according to the present invention.

The digital storage means which can particularly be a disk, a CD or a DVD, a USB flash drive, a flash card, a SD card etc., preferably comprises electrically readable control signals which can interact with a programmable computer system such that the execution of the technical steps of the method according to the present invention is prompted or induced, respectively.

Thereby, all, a few or some of the automatically performed steps of the method according to the present invention may be prompted. The latter also applies for the computer program product and the computer program.

The computer program product preferably comprises a program code stored on a machine-readable storage means for prompting the execution of the automatically performable steps of the method according to the present invention when the program product is run on a computer.

The term "machine-readable storage means" as used herein refers to a storage or data means, respectively, containing data or information that are interpretable by software and/or hardware. The storage means can be a data storage means such as a disk, a CD, DVD, a USB flash drive, a flash card, a SD card and the like.

The computer program comprises a program code for prompting the execution of the automatically performable steps of the method according to the present invention when running the program on a computer.

Certain embodiments according to the present invention comprise one or more of the following advantages.

The present invention provides a valve arrangement by means of which venting and/or flushing an extracorporeal blood circuit is possible in an advantageously simple and technically less complex manner. The valve arrangement according to the present invention can advantageously also be used for a non-occluding blood pump which has hitherto not been possible for such pumps in the field of extracorporeal blood treatments. Therewith, some of the methods mentioned above can now advantageously also be used with non-occluding blood pumps.

By means of the third valve, the separation of air out of the extracorporeal blood circuit can advantageously be performed or facilitated. During the treatment, air can penetrate into the extracorporeal blood circuit. This air is usually detected by the protective system (air bubble detector) and has to be removed from the extracorporeal blood circuit. In conventional tubing systems, this is achieved manually.

By means of automated ventilation such as is possible by means of the present invention, the effort required herefore can advantageously be minimized. In some embodiments according to the present invention, the safety of the system can be increased. This can in particular be the case when, for the purpose of venting, blood is decoupled from the patient's blood system by means of the valve block or the recirculation adaptor, respectively, preferably by correspondingly switching the third valve. Hereby, blood being present extracorporeally can be recirculated within the extracorporeal blood circuit such that air is directly guided into the air separation chamber without reaching the patient or having to be directed through the capillary filter of, e.g., a dialyzing apparatus. This can be of particular advantage as air easily "accumulates" in the capillary filter or is disintegrated to micro-bubbles. Therefore, the third valve advantageously offers the possibility to direct air bubbles present to the air separation chamber (e.g., the venous drip chamber) by means of internal circulation or recirculation in or opposite to the usual flow direction of an extracorporeal blood treatment.

The third valve can advantageously offer the possibility to recirculate the blood within the cassette while the patient is decoupled. Thereby, the patient can also be connected, if he wants to, which can advantageously save time and effort.

A recirculation within the extracorporeal blood circuit can offer the advantage that blood present extracorporeally can be further pumped across the filter in a case of, e.g., an access problem (e.g., in case of a high return pressure). In this way, in certain embodiments, it can advantageously be avoided that such an access problem will result in a stop of the flow through the extracorporeal blood circuit. This may advantageously allow for significantly reducing the risk of blood coagulation, for example, in the filter.

Furthermore, the present invention can in some of its embodiments advantageously contribute for enabling further circulation across the filter in alarm situations in which the blood pump would usually necessarily be stopped. In this way, it can advantageously be ensured for the patient not to suffer a loss of blood due to discarding the coagulated system, to achieve a more effective treatment time and to omit an optionally necessary change of the system.

When the third valve is opened for recirculation or internal circulation, respectively, in some embodiments according to the present invention, the sixth valve and, in case of air separation, the ventilation valve will be opened—if present, respectively. The first, the second, the fourth and the fifth valve should each be closed.

The sixth valve can advantageously be used for enabling filling or priming, respectively, both the arterial blood line and the venous blood line when using a non-occluding blood pump. Therefore, the arterial blood line is at first filled retrogradely, that means opposite to the usual flow direction, by means of the dialysate pump while the sixth valve is closed and, after opening the sixth valve, the venous blood line is filled anterogradely, that means in the usual flow direction, by means of the blood pump.

In case of an occluding blood pump, the sixth valve can advantageously be used for rinsing the arterial blood line upstream.

Besides the use described above, the sixth valve is analogously also used for flushing (blood return) the extracorporeal blood circuit.

The position of the sixth valve between the filter and the drip chamber can advantageously contribute for performing air separation, filling and emptying in an intended manner.

In case of need, the flow direction can advantageously be reversed or inversed, respectively, in the arterial and the venous blood line (flow reversion) by means of the first and the fourth as well as the second and the fifth valve. Thereby, the direction of the blood flow in the filter can be maintained. In this way, the counter flow principle can advantageously be maintained. Flow reversion can be of particular advantage in case of flow problems, e.g., by sucking the catheter. In certain embodiments according to the present invention, flow reversion can be induced by the dialyzing machine automatically or in a self-actuating manner (by means of corresponding devices). This may, for example, be the case if an insufficient flow is detected.

Additionally, the valve arrangement according to the present invention offers the possibility to prompt a blood return in case of a unilateral occlusion of a blood line and/or of a catheter or a needle.

The use of active valves such as provided in certain embodiments of the present invention can advantageously allow for maintaining the counter flow principle as well.

Moreover, active valves can advantageously contribute for enabling unilaterally flushing and/or unilaterally returning blood through the arterial ("access") blood line or the venous ("return") blood line of the tubing system. In this way, it can advantageously be possible to perform an automated diagnosis of the access problems (clotting/sucking the catheter) as a flow can advantageously be generated in one or even in both directions (in and opposite to the usual flow direction) in the two blood lines (the arterial and the venous blood line) in a respectively separate or independent manner.

BRIEF DESCRIPTION OF THE DRAWINGS

In the following, the present invention is exemplarily described with reference to the appended drawing. In the drawing, identical reference numerals refer to the same or identical components. In the figures.

DETAILED DESCRIPTION

The present invention can advantageously be used for a plurality of extracorporeal blood treatment methods such as, for example, a kidney support therapy, a liver support therapy, an apheresis, a transfusion and the like, in particular in methods in which the access to the patient's blood system is established by means of two connection devices such as needles or cannulae. Examples for such methods include hemodialysis, hemofiltration, hemodiafiltration or adsorption.

The present invention is in the following exemplarily described with reference to a dialyzing method without, however, intending to limit the present invention to such a method of handling or to the following embodiments in any way.

An extracorporeal blood circuit is used for performing the dialyzing method. The extracorporeal blood circuit can be designed as a tubing system. The extracorporeal blood circuit is flown through by fluids. Examples for fluids flowing through the extracorporeal blood circuit include liquids such as blood, dialysate, substituate liquid, drug solutions and the like, gases such as air, as well as combinations or mixtures thereof.

In the figures illustrated below, open or opened, respectively, valves are illustrated by a square at the valve symbol; closed valves do not show such a square.

Figure 1:
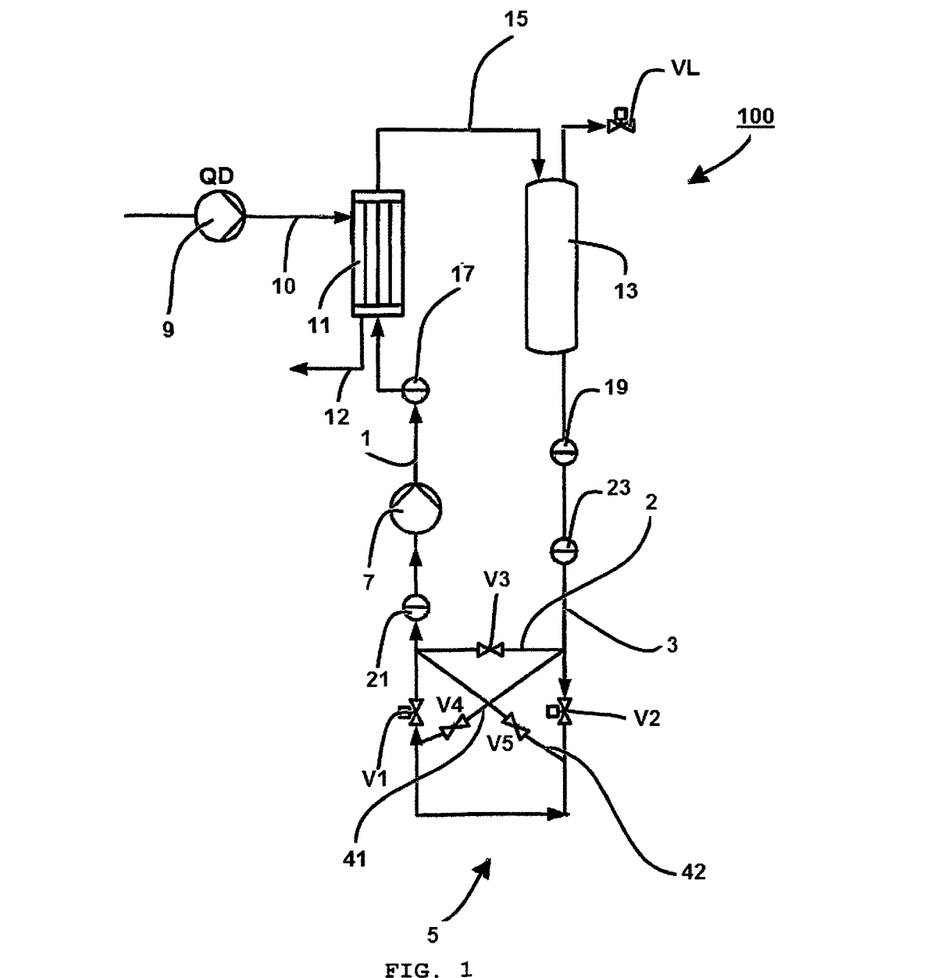
FIG. 1 shows a first valve arrangement according to the present invention during a filling process with an occluding blood pump.

FIG. 1 shows a first valve arrangement according to the present invention during a filling process with an occluding blood pump in a first filling interval or section, respectively.

The method shown in FIG. 1 can be an initial filling of an extracorporeal blood circuit 100.

The extracorporeal blood circuit 100 schematically represented in FIG. 1 comprises an arterial patient line or an arterial blood line 1, respectively, and a venous patient line or a venous blood line 3, respectively.

Patient connectors which allow for an access to a patient's vascular system for the purpose of extracorporeal blood treatment, e.g., an arterial and a venous patient access (not shown in FIG. 1) are short-circuited. As shown in FIG. 1, the patient connectors are short-circuited via a valve arrangement according to the present invention, in FIG. 1, e.g., a recirculation adaptor 5. The recirculation adaptor 5 comprises five valves such as shown in FIG. 1, namely the first valve V1, the second valve V2, the third valve V3, the fourth valve V4 and the fifth valve V5.

The first valve V1 is arranged in the arterial blood line 1, the second valve V2 is arranged in the venous blood line 3, the third valve V3 is arranged in a blood line 2 between the arterial blood line 1 and the venous blood line 3, the fourth valve V4 is arranged in a first arteriovenous blood line 41 and the fifth valve V5 is arranged in a second arteriovenous blood line 42.

In the following, the afore-mentioned valves are shortly referred to as valves from V1 to V5. Likewise, the sixth valve V6 is shortly referred to as valve V6.

A blood pump 7 is arranged in or at, respectively, the arterial blood line 3 of the extracorporeal blood circuit 100. In the embodiment of the present invention illustrated in FIG. 1, the blood pump 7 is designed as an occluding blood pump.

A dialysate circuit (indicated in FIG. 1 by a dialysate supply line 10 for fresh dialysate and a dialysate drain line 12 for used dialysate) comprises a dialysate pump 9. For performing the method described herein, the dialysate circuit can be completely filled with fluid, e.g., dialysate. It can be filled with fluid partly or in segments thereof.

The blood pump 7 conveys a flow or fluid flow QB, respectively, representing volume per time.

In the present embodiment, the blood pump 7 conveys in a direction opposite to the usual flow direction of an extracorporeal blood treatment (i.e., opposite to the direction of the arrow in FIG. 1). At the same time, the dialysate pump 9 conveys a flow or fluid flow QD, respectively, representing volume per time, wherein QD>QB, across the membrane of a filter or through the membrane, respectively, such as a membrane of a dialyzer 11.

The dialyzer 11 can be the HD 1000 S dialyzer of the company Fresenius Medical Care AG & Co. KG, Germany. However, the type and/or design of the dialyzer are not particularly limited.

QD is the flow on the dialysate side of the dialyzer 11 across the membrane into the blood compartment or to the blood side, respectively, of the extracorporeal blood circuit 100. Herefor, a balancing system (not shown in FIG. 1) has to generate a "positive" balance with a flow QD (QD>QB) accordingly.

As stated above, in some embodiments according to the present invention, the fluid flow to the patient can be higher than the fluid flow away from the patient in case of a positive balance. At a positive balance, the patient can be supplied with liquid.

The valves V1 and V2 are open, the valves V3, V4 and V5 are closed. The valves V3, V4 and V5 are not necessary or do not have to be provided, respectively, for the function of the filling process illustrated with respect to FIG. 1.

A ventilation valve VL is open which is, as shown in FIG. 1, arranged in a branch line of an air venting device such as a venous drip chamber or an air separation chamber 13, of the venous blood line 3 of the extracorporeal blood circuit 100. Other arrangements of the ventilation valve VL may be possible and are also comprised by the present invention. The ventilation valve VL can vent to an exterior of the extracorporeal blood circuit 100, in particular, e.g., to the surroundings or to the atmosphere.

The dialysate introduced across the membrane of the dialyzer 11 into the blood compartment of the extracorporeal blood circuit 100 at first displaces air in the dialyzer 11 and later on both upstream and downstream of the blood compartment of the extracorporeal blood circuit 100. The air is thereby collected and separated in the air separation chamber 13 (e.g., a venous drip chamber or a specific air separation chamber).

By suitably determining the flows QD and QB or by setting a flow difference (QD−QB), respectively, venting a blood line 15 between the dialyzer 11 and the air separation chamber 13 and the arterial and the venous blood line 1 and 3 can be achieved at the same time.

As soon as the blood lines 1, 2 and 3 and the air separation chamber 13 are filled with fluid, the first filling interval is finished.

In a second filling interval of the method (not shown in FIG. 1), at first the dialysate pump 9 is stopped or the balancing system is set to neutral balance, respectively, and the ventilation valve VL is closed.

As stated above, at a neutral balance, the fluid flow to the patient can be as high as the fluid flow away from the patient. The patient's weight can thus be maintained constantly.

The fluid (e.g., dialysate) is circulated within the extracorporeal blood circuit 100 by means of the blood pump 7 while the valves V1 and V2 are still open. Thereby, the blood pump 7 conveys in the usual flow direction (in the direction of the arrow shown in FIG. 1).

Thereby, the remaining air present in the extracorporeal blood circuit 100 is directed into the air separation chamber 13 and "collected" there.

If the fluid level in the air separation chamber 13 has dropped, air can be removed therefrom. Therefor, a positive balance (QD>0) is set in the balancing system, the ventilation valve VL is opened and (preferably) the blood pump 7 is stopped.

Thereby, the fluid is directed out of the dialyzer 11 via the blood line 15 between the dialyzer 11 and the air separation chamber 13 into the air separation chamber 13. It displaces the air out of the air separation chamber 13.

In case of need, the second filling interval can be repeated for arbitrary times such that advantageously also larger amounts of air can be removed from the extracorporeal blood circuit 100.

As further shown in FIG. 1, the extracorporeal blood circuit 100 comprises a sensor 17 for measuring the arterial pressure in front of the dialyzer 11 ("pre filter pressure"), a sensor 19 for measuring the venous pressure downstream the air separation chamber 13 ("pressure return"), a first multi-sensor 21 in the arterial blood line 1 and a second multi-sensor 23 in the venous blood line 3.

The first multi-sensor 21 can be a sensor for detecting only one the following parameters or an (integrated) sensor for simultaneously detecting several parameters such as the arterial pressure ("pressure access"), the optical density (OD) and the like and/or for detecting air bubbles optionally present in a blood line interior of the arterial blood line 1 (air bubble detector, ABD).

The second multi-sensor 23 can be a sensor for detecting only one the following parameters or an (integrated) sensor for simultaneously detecting several parameters such as the venous pressure, the optical density (OD) and the like and/or for detecting air bubbles optionally present in a blood line interior of the venous blood line 3 (air bubble detector, ABD).

Figure 2:
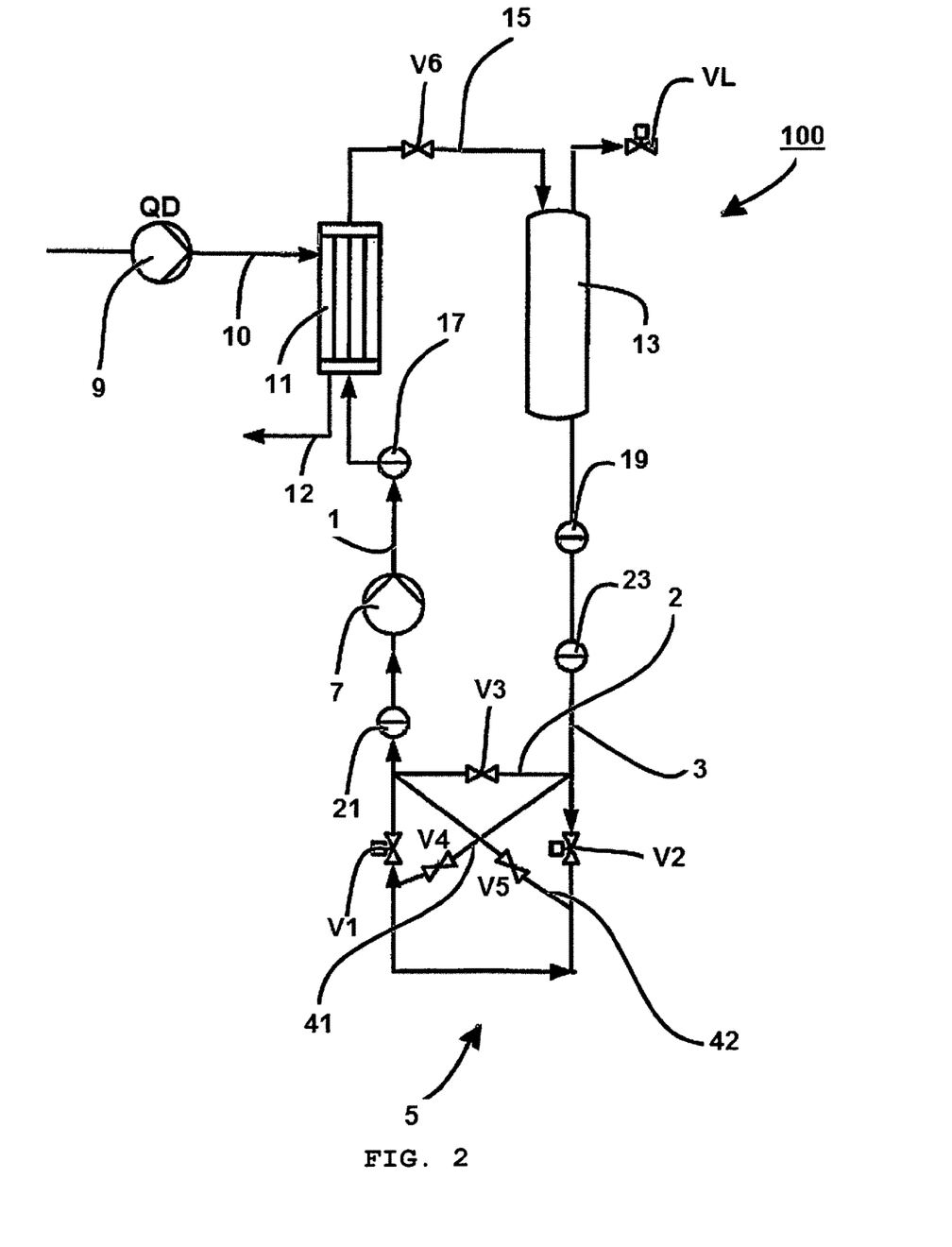
FIG. 2 shows a second valve arrangement according to the present invention during a filling process with a non-occluding blood pump.

FIG. 2 shows a second valve arrangement according to the present invention for performing a filling process with a non-occluding blood pump in a first filling interval. Accordingly, the blood pump 7 is designed as a non-occluding pump in FIG. 2, e.g., as a centrifugal pump or a rotary pump or an impeller pump.

For also performing the method illustrated with respect to FIG. 2, patient connectors (not shown in FIG. 2) are short-circuited by means of the recirculation adaptor 5. The dialysate circuit (indicated in FIG. 2 by means of the dialysate supply line 10 and the dialysate drain line 12) is filled with fluid.

The valve arrangement shown in FIG. 2 substantially corresponds to the representation of FIG. 1. In addition to the arrangement shown in FIG. 1, in the arrangement of FIG. 2, an additional valve V6 is arranged in the blood line 15 between the dialyzer 11 and the air separation chamber 13.

In a state of stagnation, a non-occluding blood pump 7 can be through-flown or overflown by a fluid or a liquid, respectively, in a free manner. For such a blood pump 7, a reversion of the flow direction is usually not possible. By using such a blood pump 7, the filling process may be carried out as stated below:

Analogously to the performance of FIG. 1, fluid is introduced into the extracorporeal blood circuit 100 from the dialysate circuit by setting a positive balance. In the first filling interval, the blood pump 7 is stopped.

At first, the valve V6 is closed, the valves V1 and V2 and the ventilation valve VL are open. The valves V3, V4 and V5 are closed. The method described here can also be carried out without using the valves V3, V4 and V5.

Fluid is pressed out of the dialysate compartment across the membrane of the dialyzer 11 onto the blood side of the dialyzer 11 and flows through the blood pump 7 and the arterial blood line 1 and the venous blood line 3 into the air separation chamber 13.

As soon as a fluid level has been detected in the air separation chamber 13, valves V1 and V2 are closed, valve V6 is opened. Now, fluid can flow through the blood line 15 into the air separation chamber 13 and displace the air. Therewith, the first filling interval is finished.

In the second filling interval (not shown in FIG. 2), at first the dialysate pump 9 is stopped or the balancing system (not shown in FIG. 2) is set to neutral balance, respectively. Ventilation valve VL is closed.

The fluid is circulated within the extracorporeal blood circuit 100 by means of the blood pump 7 while the valves V1, V2 and V6 are open. Thereby, the remaining air in the extracorporeal blood circuit 100 is directed into the air separation chamber 13 and "collected" there.

If or when the fluid level in the air separation chamber has dropped, air can be removed therefrom. Therefor, a positive balance is set in the balancing system (i.e. QD>0). The ventilation valve VL is opened. The blood pump 7 is preferably stopped.

Thus, fluid is directed out of the dialyzer 11 via the blood line 15 between the dialyzer 11 and the air separation chamber 13 into the air separation chamber 13. It displaces the air out of the air separation chamber 13.

In case of need, the second filling interval can be repeated for arbitrary times such that advantageously also larger amounts of air can be removed from the extracorporeal blood circuit 100.

Figure 3:
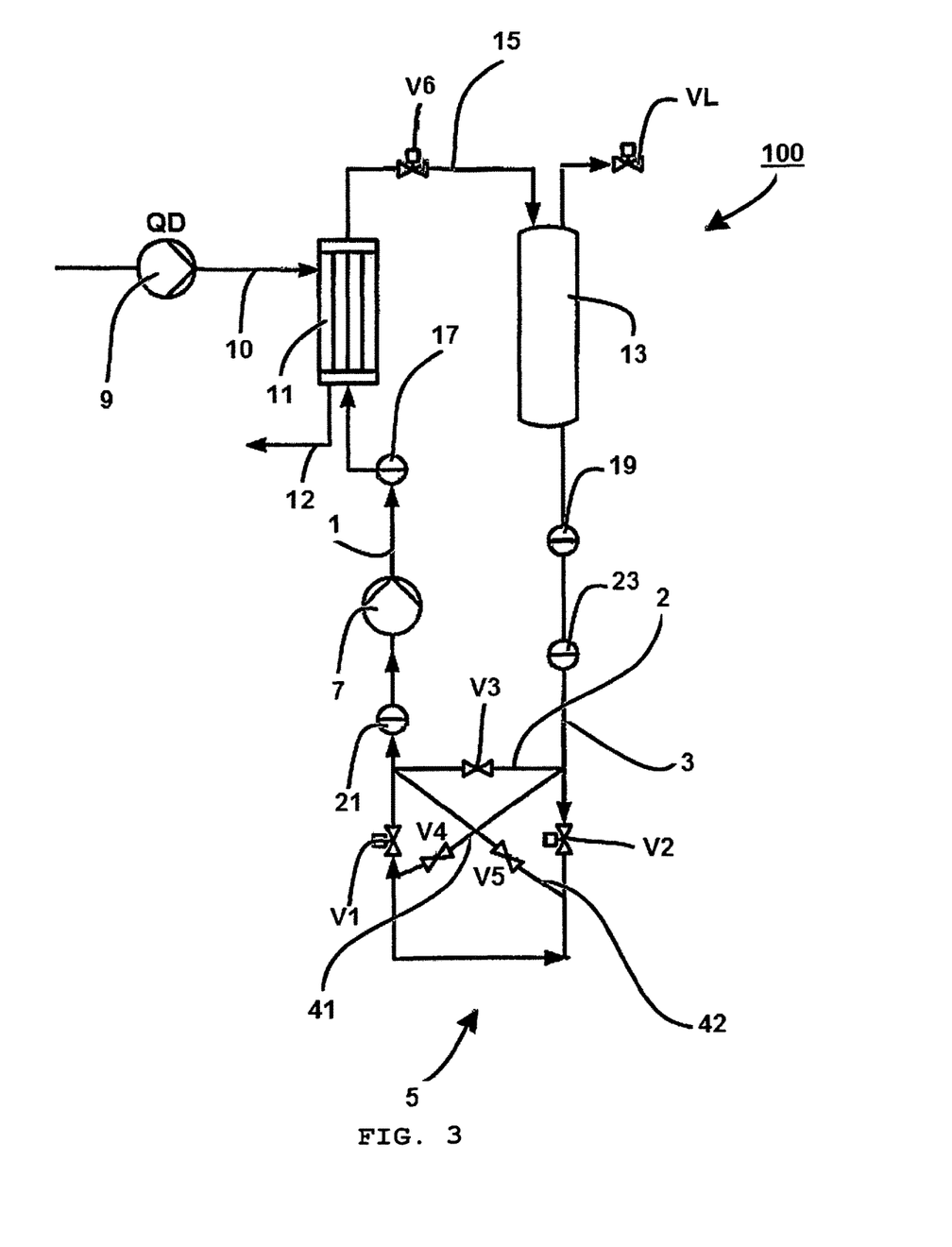
FIG. 3 shows the second valve arrangement according to the present invention during a filling process for flushing blood lines.

FIG. 3 again shows the valve arrangement according to the present invention of FIG. 2. With reference to FIG. 3, a process for flushing blood lines in the case that a flow problem is present in at least one of the blood lines is described in the following.

Flushing without flow problems can correspond to the "normal" process upon disconnecting a patient.

The blood lines, i.e. the arterial blood line 1 and the venous blood line 3, are connected with the vascular access of the patient, e.g., a shunt or a fistula. The blood pump 7 conveys with a flow QB in a direction opposite to the usual flow direction (as indicated by the direction of the arrow in FIG. 3).

At the same time, the dialysate pump 9 conveys fluid with a flow QD (wherein QD>QB, positive balance) out of the dialysate circuit (indicated in FIG. 3 by means of the dialysate supply line 10 and the dialysate drain line 12) across the membrane of the dialyzer 11 into the extracorporeal blood circuit 100.

The valves V1, V2 and V6 are open. The valves V3, V4 and V5 and the ventilation valve VL are closed. Therewith, blood is contemporarily displaced out of the dialyzer 11 via the arterial blood line 1, the venous blood line 3 and the blood line 15 by means of the fluid and returned to the patient. By means of the multi-sensors 21 and 23, it can be determined when the fluid displaces or has sufficiently displaced the blood.

The blood return process can thereby, for example, be controlled either by means of regulating the flow difference (QD−QB) between the flow QD of the dialysate pump 9 and the flow QB of the blood pump or by switching the valves V1 and V2.

When using a non-occluding blood pump 7, the said will be stopped during the (blood) return process and blood is displaced out of the two blood conducting branches, i.e., the arterial blood line 1 and the venous blood line 3, including the blood line 15 (between the dialyzer 11 and the air separation chamber 13), by means of the fluid coming from the dialysate compartment; and returned to the patient. The order of the return process from the arterial blood line 1 and the venous blood line 3/blood line 15 may be selected arbitrarily. The return process is determined by switching the valves V1 and V2.

In the embodiment of the method described with reference to FIG. 3, valve V3 is regularly closed. In this method, valve V3 can be used, for example, in a case of decoupling the patient or bypassing the patient, respectively, or excluding the patient from the circulation through the extracorporeal blood circuit (i.e., valve V3 is open and the valves V1, V2, V4 and V5 are closed), e.g., in order to separate air.

In another embodiment of the method according to the present invention which is not illustrated by way of another figure here, an extracorporeal blood circuit is flushed in case of a blockage of one of the two blood lines as is described in the following. For better understanding the cooperation of the single components, it is referred to the representation of the extracorporeal blood circuit 100 with respect to the FIGS. 1 to 3.

This flushing process can be used when either at least one of the two blood lines or one of the catheter legs is blocked. In case of a blockage, the flushing process advantageously allows for an at least partly performed blood return which is not or only limitedly possible with usual methods.

For the performance of the flushing process in the embodiment described here, the valves V3 and V6 are necessary.

The blood lines, i.e. the arterial blood line 1 and the venous blood line 3, are respectively connected with the corresponding vascular access of the patient.

The blood pump 7 conveys with a flow QB in a direction opposite to the usual flow direction. At the same time, the dialysate pump 9 conveys fluid with a flow QD, wherein QD>QB (positive balance), out of the dialysate circuit across the membrane of the dialyzer 11 into the extracorporeal blood circuit 100.

By means of the valve block (V1 to V5), i.e. the recirculation adaptor 5, the entire flow can be put or directed to one of the two blood lines. If, for example, the arterial catheter leg is blocked, the blood return process can be carried out via the venous blood line 3: The valves V1, V3 and V4 and the ventilation valve VL are thereby closed, valves V2 and V5 are open. The fluid displaces the blood i.a. out of the dialyzer 11 and the venous air separation chamber 13 and is returned to the patient via the free blood line (in the example chosen the venous blood line 3). In this way, a loss of blood in case of blockage of one blood line can advantageously be minimized. By switching the valves V5 and V6 or by suitably selecting the flow difference QD−QB, respectively, the two branches or blood lines, respectively,— the arterial blood line 1 and the venous blood line 3/blood line 15—(upstream and downstream the dialyzer 11) can be flushed.

In another possible embodiment, blood can alternatively also be returned to the patient while the blood pump 7 stagnates (preferably with flow QD of the dialysate pump 9 alone). This substantially relates to blood downstream the dialyzer 11. This embodiment can be reasonable if or when the dialyzer's 11 inlet is blocked. If only the inlet of the dialyzer is blocked, both blood lines (the arterial blood line 1 and the venous blood line 3/the blood line 15) could subsequently be flushed by correspondingly switching the recirculation adaptor 5.

In another possible embodiment of the method according to the present invention, blood can alternatively be returned to the patient by using identical pump flow rates QD, QB, i.e. it approximately or exactly applies: QD=QB. Hereby, the blood pump 7 rotates in the reverse direction. Only the part upstream the dialyzer 11 will be flushed. This can be of advantage when a blockage is present between the outlet of the dialyzer 11 and the recirculation adaptor 5.

In another possible embodiment of the method according to the present invention, the two legs (the arterial blood line 1 and the venous blood line 3/the blood line 15) (upstream and downstream the dialyzer 11) can alternatively be flushed subsequently when using a non-occluding blood pump 7. Herefor, a positive balance (i.e. QD>QB) is set again and thus fluid is conveyed across the membrane of the dialyzer 11 into the extracorporeal blood circuit 100. By adequately switching the flow paths by means of the valves V1 to V6, the non-blocked blood lines can be flushed subsequently (analogously to the three embodiments described above).

Figure 4:
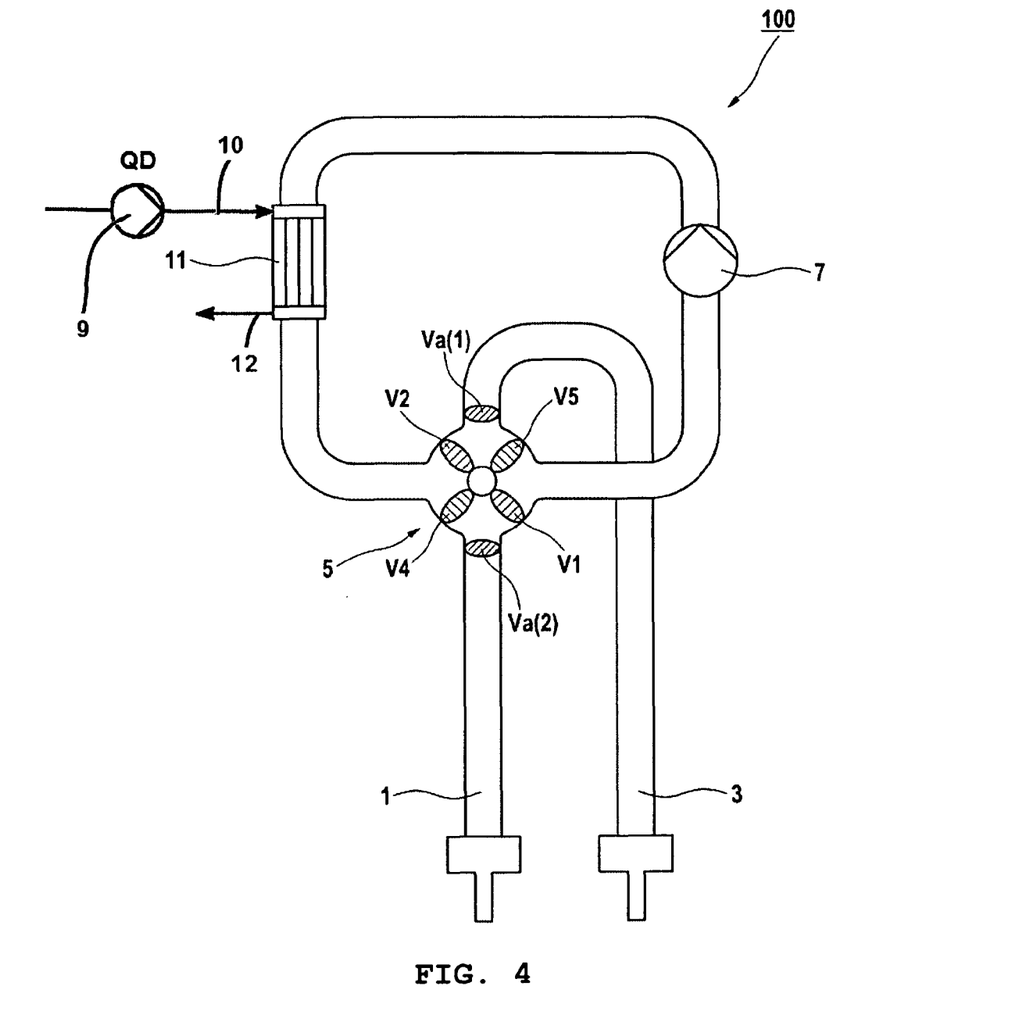
FIG. 4 schematically shows a valve arrangement according to the present invention in a first embodiment.
Figure 5:
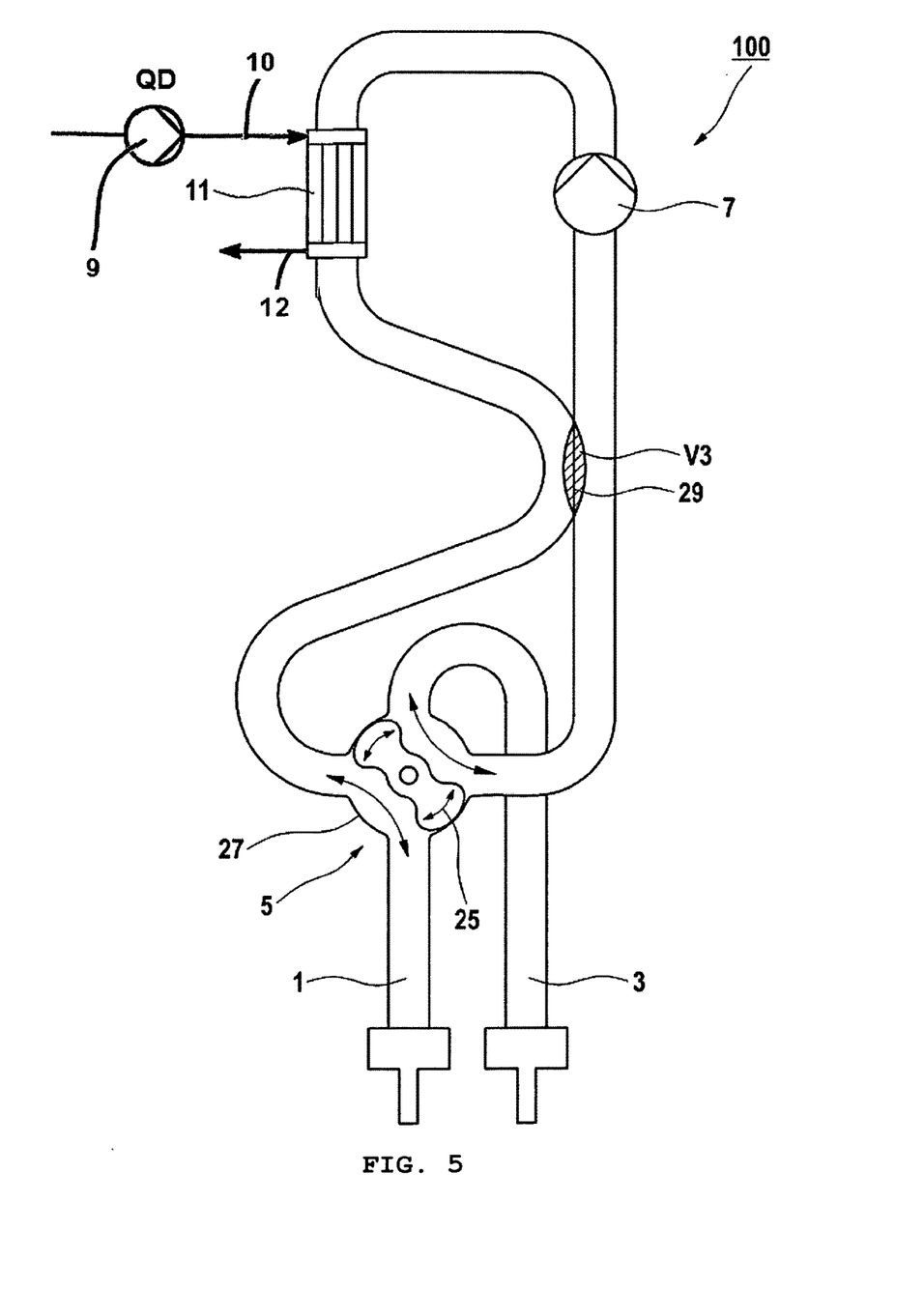
FIG. 5 schematically shows a valve arrangement according to the present invention in a second embodiment.
Figure 6:
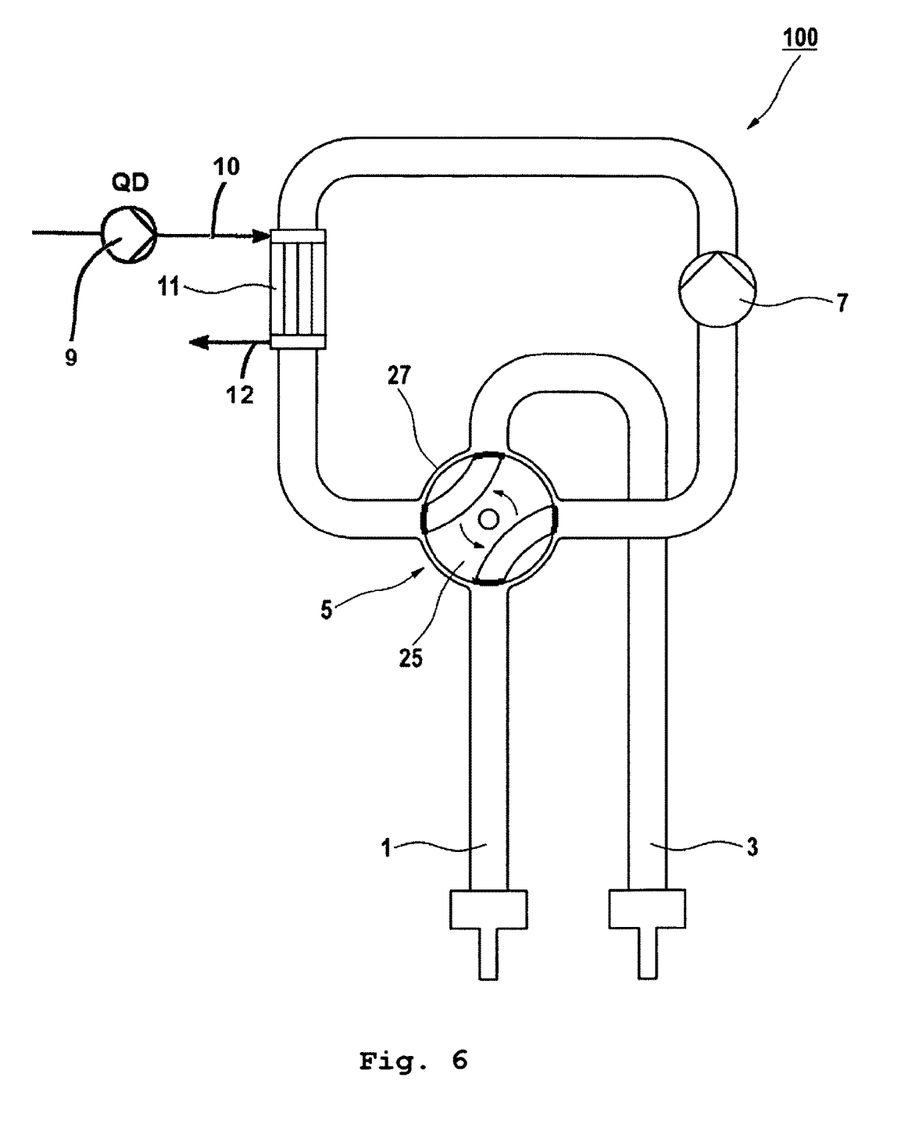
FIG. 6 schematically shows a valve arrangement according to the present invention in a third embodiment.

FIGS. 4 to 6 exemplarily show schematic embodiments of a recirculation adaptor 5 representing an example for a valve arrangement according to the present invention.

The recirculation adaptor 5 or valve block can be part of a blood cassette, e.g., in form of a disposable or of a disposable cassette.

In particular, all valves mentioned above, specifically the valves V1 to V5, can be part of or integrated within a disposable.

However, the present invention is not limited in that all or some of the valves have to be arranged on or in a recirculation adaptor 5 such as shown in the example of the figures. They can also be realized without a means having the form of an adaptor.

In the embodiments shown in FIGS. 4 to 6, the non-switched fluid paths are preferably completely or substantially free from dead spaces such that advantageously no blood or no coagulation relevant blood volume is present or locked in, e.g., a valve or a tube segment. The entire valve space can always be freely flushable with flowing blood. This can advantageously contribute to minimizing or excluding the risk of clotting.

In the example of FIG. 4, the valve functions of the valves V1, V2, V4 and V5 are directly represented by means of single separated valves (same denotation of the valves and the valve functions). These four valves can be used for switching the flow paths. In certain embodiments according to the present invention, the valves can each be switchable independently from each other. This can have the advantage that arbitrary flow paths can be switched by means of this arrangement. The single valves can thereby, e.g., be membrane valves. The valves can be designed as described in document DE 100 46 651 A1 or in document DE 102 39 597 A1. The entire contents of the afore-mentioned documents are herewith fully enclosed by way of reference.

All or some of the valves can be active valves. In some embodiments according to the present invention, the valves are provided for being controlled automatically. They can comprise a corresponding controlling means or device, respectively. In certain embodiments, these valves are not manually actuable or are not used as such. In some embodiments according to the present invention, the valves are not designed as non-return valves.

The function of the valve V3 not shown in FIG. 4 is achieved by either V2 or V5 being open and Va(1), V1 and V4 being closed or, alternatively, V1 and V4 being open and Va(2), V2 and V5 being closed. Valves Va(1) and Va(2) can be present in one body, but this does not have to be the case.

This arrangement can be an integral constituent of a cassette and/or a disposable as well.

Valve V3 can be a phantom valve. A "phantom valve" as used herein can be an element comprising an actuator surface (for example, an actuator membrane) reachable by means of an actuator, which can fulfill the function of a valve as explained above. Examples of appropriate phantom valves can be derived from the afore-mentioned applications of the present applicant DE 10 2009 024 664.6, DE 10 2009 024 468.9-41 and DE 10 2009 012 632.5-41.

As regards their construction, the valves Va(1) and Va(2) can be designed analogously to the valves described in document DE 100 46 651 A1 or DE 102 39 597 A1. The entire contents of the documents cited are herewith fully incorporated by way of reference.

In the embodiment of the recirculation adaptor 5 shown in FIG. 5, the valve functions of the valves V1, V2, V4 and V5 are represented by means of a rotary element or a rotational element 25. In FIG. 5, the rotatability of element 25 is indicated by means of the bended double arrows in the recirculation adaptor 5. By rotating element 25 by predetermined angles in a housing 27, flow paths can correspondingly be switched or blocked, respectively, or released, optionally comprising intermediate levels or positions between an open and a closed state. For the function of valve V3, in the example of FIG. 5 which is not intended to be understood as limiting, the flow paths of the lines to the dialyzer 11 and to the blood pump 7 are combined or connected such that they are merely separated by a, preferably simple, bar 29. By means of an element of valve V3 sealing or releasing the connection of the two lines via the bar 29, the function of short-circuiting of valve V3 can be represented.

In the embodiment shown in FIG. 6, the functions of the valves V1, V2, V4 and V5 are enabled by means of the rotatable element 25. FIG. 6 shows an alternative embodiment of the rotatable element 25 of FIG. 5. The valve function of valve V3 could alternatively be designed analogously to the embodiment of the afore-mentioned exemplary embodiment of FIG. 5.

Reference numeral list

| reference numeral | description |
|---|---|
| 100 | extracorporeal blood circuit |
| 1 | arterial blood line |

-continued

Reference numeral list

| reference numeral | description |
|---|---|
| 2 | blood line between the arterial blood line and the venous blood line |
| 3 | venous blood line |
| 41 | first arteriovenous blood line |
| 42 | second arteriovenous blood line |
| 5 | recirculation adaptor |
| 7 | blood pump |
| 9 | dialysate pump |
| 10 | dialysate supply line |
| 11 | dialyzer |
| 12 | dialysate drain line |
| 13 | air separation chamber |
| 15 | blood line between dialyzer and air separation chamber |
| 17 | sensor for measuring the arterial pressure in front of the dialyzer |
| 19 | sensor for measuring the venous pressure behind the air separation chamber |
| 21 | first multi-sensor in the arterial line |
| 23 | second multi-sensor in the venous line |
| 25 | rotatable element |
| 27 | housing |
| 29 | bar |
| V1 | valves |
| V2 | |
| V3 | |
| V4 | |
| V5 | |
| V6 | |
| Va(1) | |
| Va(2) | |
| VL | ventilation valve |
| QB | flow of the blood pump |
| QD | flow of the dialysate pump |

What is claimed is:

1. A system having a valve arrangement for use with an extracorporeal blood circuit, the valve arrangement comprising:
a first valve arranged along an arterial blood line of the extracorporeal blood circuit, wherein the arterial blood line is arranged to conduct blood being drawn from a patient for an extracorporeal treatment;
a second valve arranged along a venous blood line of the extracorporeal blood circuit, wherein the venous blood line is arranged to conduct treated blood being returned to the patient,
wherein the extracorporeal blood circuit defines a fluid flow loop extending from a downstream side of the first valve to an upstream side of the second valve;
a first arteriovenous line connected to the arterial blood line upstream of the first valve and to the venous blood line upstream of the second valve;
a second arteriovenous line connected to the arterial blood line downstream of the first valve and to the venous blood line downstream of the second valve;
a third arteriovenous line connected to the arterial blood line downstream of the first valve and to the venous blood line upstream of the second valve;
a third valve arranged along the third arteriovenous line;
a fourth valve arranged along the first arteriovenous line; and
a fifth valve arranged along the second arteriovenous line.

2. The system according to claim 1, wherein the system further comprises at least one of: a dialyzer, a blood pump, a measuring sensor, and a chamber arranged along the fluid flow loop.

3. The system according to claim 1, wherein the system further comprises a sixth valve which is connected to a blood treatment device and to an air venting device of the extracorporeal blood circuit.

4. The system according to claim 3, further comprising a ventilation valve configured to establish a connection between an interior of the extracorporeal blood circuit and an exterior thereof.

5. The system according to claim 4, wherein at least one valve selected from the group consisting of the first valve, the second valve, the third valve, the fourth valve, the fifth valve, the sixth valve, and the ventilation valve is an active or controlled valve.

6. The system according to claim 4, further comprising a device configured to control or regulate a valve function of at least one valve selected from the group consisting of the first valve, the second valve, the third valve, the fourth valve, the fifth valve, the sixth valve, and the ventilation valve.

7. The system according to claim 1, wherein at least the first valve, the second valve, the fourth valve, and the fifth valve are present in a common support material.

8. The system according to claim 1, wherein at least the third valve is a phantom valve.

9. The system according to claim 1, further comprising sensors configured to detect at least one of an optical density, an arterial or venous pressure, or air inclusions.

10. The system according to claim 1, further comprising
a device configured to control or regulate a flow difference
between a flow of a blood pump and a flow of a dialysate pump, wherein the flow difference is generated by a system configured to operate the blood pump or the dialysate pump.

11. The system according to claim 1, wherein at least two or more valves are designed or embodied as a segment of a rotational element which is configured to be switchable by rotation of the rotational element.

12. The system of claim 1, wherein the system is configured as a blood tubing set.

13. The system of claim 1, wherein the system is configured as a blood cassette.

14. The system of claim 1, wherein the system is configured as a treatment apparatus configured to treat medical fluids, wherein the system further comprises at least one controlling device and actuators that are configured to control or regulate the valve arrangement.

15. The system according to claim 14, wherein the system is configured as an apparatus for extracorporeal blood treatment.

16. A method for handling an extracorporeal blood circuit, the method comprising using the system according to claim 4.

17. The method according to claim 16, further comprising establishing fluid communication between the arterial blood line and the venous blood line by opening the third valve, wherein the opening the third valve short-circuits the fluid flow loop.

18. The method according to claim 16, said method being for filling the extracorporeal blood circuit or parts thereof using a non-occluding blood pump, said method further comprising at least one step selected from the group consisting of:
a) short-circuiting patient connectors;
b) introducing fluid from a dialysate circuit into the extracorporeal blood circuit by setting a positive balance;
c) stopping the blood pump;

d) closing a sixth valve, opening the first and the second valves and the ventilation valve;

e) closing the third, the fourth and the fifth valve;

f) pressing fluid out of the dialysate compartment across the membrane of the filter onto the blood side of the filter;

g) closing the first and the second valve and opening the sixth valve after having detected a fluid level in the air separation chamber;

h) at least one of stopping the dialysate pump or setting a balancing system to a neutral balance;

i) closing the ventilation valve;

j) circulating the fluid within the extracorporeal blood circuit by use of the blood pump while the first and the second valve and the sixth valve are open;

k) setting a positive balance in the balancing system with the flow rate of a dialysate being greater than zero;

l) opening the ventilation valve; and m) stopping the blood pump.

19. The method according to claim 18, comprising the further step of:

n) performing the method steps h) to m) according to claim 18 for several times.

20. The method according to claim 16, said method being for flushing the extracorporeal blood circuit or parts thereof while no flow disturbance is present in one of the blood lines, said method further comprising at least one step selected from the group consisting of:

a) conveying a flow by use of the blood pump in a direction opposite to the usual flow direction while the arterial and the venous blood line are connected with the vascular access of the patient;

b) conveying fluid by use of the dialysate pump with a flow out of the dialysate circuit, wherein the flow is larger than a flow conveyed by use of the blood pump, across the membrane of a filter of a blood treatment apparatus into the extracorporeal blood circuit;

c) opening the first, the second and the sixth valve while the third, the fourth and the fifth valve as well as the ventilation valve are or remain being closed;

d) determining, by use of sensors, when or that fluid displaces or has sufficiently displaced blood out of certain parts of the extracorporeal blood circuit;

e) controlling or regulating a blood return process according to the amount of the flow difference between the flow of the blood pump and the flow of the dialysate pump or by switching the first and the second valve;

f) stopping the non-occluding blood pump; and g) switching the first and the second valve in order to prompt the blood return to the patient via a selected one of the blood lines.

21. The method according to claim 16, said method being for flushing an extracorporeal blood circuit or parts thereof while a flow disturbance is present in one of the blood lines, said method further comprising at least one step selected from the group consisting of:

a) conveying by use of the blood pump with a flow in a direction opposite to the usual flow direction, wherein at least one of the arterial blood line or the venous blood line are each connected with the respective vascular access of the patient;

b) conveying fluid out of the dialysate circuit across the membrane of a filter of a blood treatment apparatus into the extracorporeal blood circuit by use of the dialysate pump with a flow which is larger than a flow conveyed by use of the blood pump;

c) directing the entire flow to one of the two blood lines by correspondingly switching the first, the second, the third, the fourth and the fifth valve;

d) switching the fifth and the sixth valve or adequately selecting or adjusting the flow difference between the flow of the dialysate pump and the flow of the blood pump for achieving a flow-through of the arterial blood line or the venous blood line.

22. The method according to claim 21, further comprising the step of:

e) generating a flow within the extracorporeal blood circuit by use of the dialysate pump while the blood pump does not convey or stagnates or is not overflown.

23. The method according to claim 22, further comprising the step of:

f) conveying by use of the blood pump and by use of the dialysate pump with identical pump flow rates, wherein the blood pump rotates or conveys in reverse direction.

24. The method according to claim 23, further comprising at least one step selected from the group consisting of:

g) setting a positive balance when using a non-occluding blood pump; and h) switching the flow paths by use of at least one of the first, the second, the third, the fourth, the fifth or the sixth valve for flushing the non-blocked blood lines.

25. A non-transitory computer-readable storage medium with an executable program stored thereon, wherein the program instructs a programmable computer system to execute the steps of the method according to claim 16.

* * * * *